United States Patent
Ritter

(10) Patent No.: US 7,943,723 B2
(45) Date of Patent: *May 17, 2011

(54) PROCESS FOR THE SYNTHESIS OF ETHERS OF AROMATIC ACIDS

(75) Inventor: Joachim C. Ritter, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 46 days.

This patent is subject to a terminal disclaimer.

(21) Appl. No.: 12/518,167

(22) PCT Filed: Dec. 18, 2007

(86) PCT No.: PCT/US2007/025918
§ 371 (c)(1),
(2), (4) Date: Jun. 8, 2009

(87) PCT Pub. No.: WO2008/082551
PCT Pub. Date: Jul. 10, 2008

(65) Prior Publication Data
US 2010/0048856 A1 Feb. 25, 2010

Related U.S. Application Data

(60) Provisional application No. 60/876,571, filed on Dec. 21, 2006.

(51) Int. Cl.
*C08G 64/00* (2006.01)
*C08G 63/02* (2006.01)

(52) U.S. Cl. ........... 528/206; 528/70; 528/392; 528/397

(58) Field of Classification Search .................... 528/70, 528/392, 397
See application file for complete search history.

(56) References Cited

U.S. PATENT DOCUMENTS

| 3,047,536 A | 7/1962 | Gordon |
| 3,227,680 A | 1/1966 | Tamblyn et al. |
| 4,086,350 A * | 4/1978 | Zirkle ........................ 514/320 |
| 5,674,969 A | 10/1997 | Sikkema et al. |
| 7,683,157 B2 | 3/2010 | Allen et al. |

FOREIGN PATENT DOCUMENTS

| AT | 265244 | 10/1968 |
| WO | 2006104974 A1 | 10/2006 |

OTHER PUBLICATIONS

John Goodell et al. "Synthesis and evaluation of acridine-acridone based anti-herpes agents with topoisomerase activity" Biorganic and Medicinal Chemistry, vol. 14, May 19, 2006 pp. 5467-5480.*
Beers et al., "Title of Article", High Performance Fibres (2000), pp. 93-155.
Sasson et al., Liquid-Phase Oxidation of Deactivated Methylbenzenes by Aqueous Sodium Hypochlorite Catalyzed by Ruthenium Salts Under Phase-Transfer Catalytic Conditions, J. Org. Chem., vol. 51 (1986), pp. 2880-2883.
Wu et al., Hydrogen Bond-Induced Rigid Oligoanthranilamide Ribbons That Are Planar And Straight, Organic Letters, vol. 6, No. 2 (2004), pp. 229-232.

* cited by examiner

*Primary Examiner* — Terressa M Boykin

(57) ABSTRACT

The inventions disclosed herein include processes for the preparation of an ether of an aromatic acid, processes for the preparation of products into which such an ether can be converted, the use of such processes, and the products obtained and obtainable by such processes. A key feature of the processes described is the use of a solvent comprising an alcohol ROH and an alcoholate $RO^-M^+$.

20 Claims, No Drawings

PROCESS FOR THE SYNTHESIS OF ETHERS OF AROMATIC ACIDS

This application claims the benefit of U.S. Provisional Application No. 60/876,571, filed 21 Dec. 2006, which is incorporated in its entirety as a part hereof for all purposes.

TECHNICAL FIELD

This invention relates to the manufacture of ethers of hydroxy aromatic acids, which are valuable for a variety of purposes such as use as intermediates or as monomers to make polymers.

BACKGROUND

Ethers of aromatic acids are useful as intermediates and additives in the manufacture of many valuable materials including pharmaceuticals and compounds active in crop protection, and are also useful as monomers in the production of high-performance rigid rod polymers, for example, linear rigid oligoanthranilamides for electronic applications [Wu et al, *Organic Letters* (2004), 6(2), 229-232] and polypyridobisimidazoles and the like [see e.g. Beers et al, *High-Performance Fibres* (2000), 93-155].

Existing processes to produce 2,5-dialkoxy- and 2,5-diarenoxyterephthalic acid involve stepwise alkylation of 2,5-dihydroxyterephthalic acid to form the corresponding 2,5-alkoxy- and 2,5-diarenoxyterephthalic esters followed by dealkylation of the ester to the acid. An n-hydroxy aromatic acid may be converted to an n-alkoxy aromatic acid by contacting the hydroxy aromatic acid under basic conditions with an n-alkyl sulfate. One suitable method of running such a conversion reaction is as described in Austrian Patent No. 265,244. Yields are moderate to low, productivity is low and a two-step process is necessary.

A need therefore remains for a process by which ethers of aromatic acids can be produced economically and with high yields and high productivity in small- and large-scale operation, and in batch and continuous operation.

SUMMARY

The inventions disclosed herein include processes for the preparation of an ether of an aromatic acid, processes for the preparation of products into which such an ether can be converted, the use of such processes, and the products obtained and obtainable by such processes.

One embodiment of the processes hereof provides a process for preparing an ether of an aromatic acid, the ether being described by the structure of Formula I

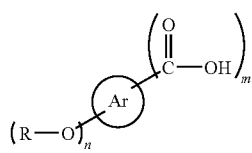

wherein Ar is a $C_6$–$C_{20}$ monocyclic or polycyclic aromatic nucleus, R is a univalent organic radical, n and m are each independently a nonzero value, and n+m is less than or equal to 8; comprising (a) contacting a halogenated aromatic acid such as is described by the structure of Formula II

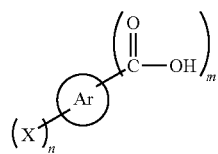

wherein each X is independently Cl, Br or I, and Ar, n and m are as set forth above, with (i) a polar protic solvent, a polar aprotic solvent or an alcoholic solvent containing the alcoholate $RO^-M^+$ (wherein M is Na or K), wherein the polar protic solvent, polar aprotic solvent or alcoholic solvent is either ROH or is a solvent that is less acidic than ROH;
(ii) a copper (I) or copper (II) source; and
(iii) a ligand that coordinates to copper, wherein the ligand comprises a Schiff base; to form a reaction mixture;

(b) heating the reaction mixture to form the m-basic salt of the product of step (a), as described by the structure of Formula III;

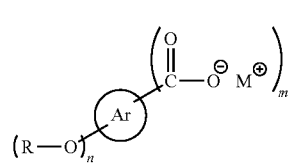

(c) optionally, separating the Formula III m-basic salt from the reaction mixture in which it is formed; and
(d) contacting the Formula III m-basic salt with acid to form therefrom an ether of an aromatic acid.

Another embodiment of this invention provides a process for preparing a compound, monomer, oligomer or polymer by preparing an ether of an aromatic acid that is described generally by the structure of Formula I, and then subjecting the ether so produced to a reaction (including a multi-step reaction) to prepare therefrom a compound, monomer, oligomer or polymer.

DETAILED DESCRIPTION

This invention provides a process having improved yield and productivity for preparing an ether of an aromatic acid, the ether being described by the structure of Formula I

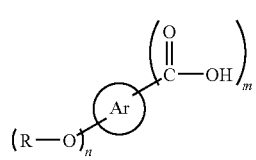

wherein Ar is a $C_6$–$C_{20}$ monocyclic or polycyclic aromatic nucleus, R is a univalent organic radical, n and m are each independently a nonzero value, and n+m is less than or equal to 8.

One embodiment of the processes hereof proceeds by (a) contacting a halogenated aromatic acid such as is described by the structure of Formula II

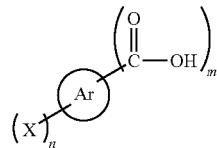

II wherein each X is independently Cl, Br or I, and Ar, n and m are as set forth above, with (i) a polar protic solvent, a polar aprotic solvent or an alcoholic solvent containing the alcoholate $RO^-M^+$ (wherein M is Na or K), wherein the polar protic solvent, polar aprotic solvent or alcoholic solvent is either ROH or is a solvent that is less acidic than ROH;

(ii) a copper (I) or copper (II) source; and (iii) a ligand that coordinates to copper, wherein the ligand comprises a Schiff base; to form a reaction mixture;

(b) heating the reaction mixture to form the m-basic salt of the product of step (a), as described by the structure of Formula III;

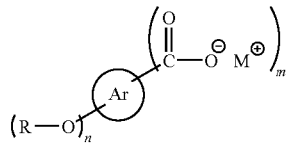

III (c) optionally, separating the Formula III m-basic salt from the reaction mixture in which it is formed; and (d) contacting the Formula III m-basic salt with acid to form therefrom an ether of an aromatic acid.

In Formulae I, II and III, Ar is a $C_6$~$C_{20}$ monocyclic or polycyclic aromatic nucleus; n and m are each independently a nonzero value and n+m is less than or equal to 8; R is a univalent organic radical; and in Formula II, each X is independently Cl, Br or I.

The radical denoted by

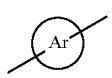

is an n+m valent $C_6$~$C_{20}$ monocyclic or polycyclic aromatic nucleus formed by the removal of n+m hydrogens from different carbon atoms on the aromatic ring, or on the aromatic rings when the structure is polycyclic. The radical "Ar" may be substituted or unsubstituted; when unsubstituted, it contains only carbon and hydrogen.

One example of a suitable Ar group is phenylene, as shown below, wherein n=m=1.

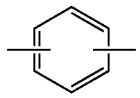

A preferred Ar group is shown below, wherein n=m=2.

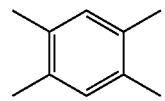

The univalent radical R is a univalent organic radical. Preferably, R is a $C_1$~$C_{12}$ alkyl group or an aryl group. More preferably, R is a $C_1$~$C_4$ alkyl group or phenyl. Examples of particularly suitable R groups include without limitation methyl, ethyl, i-propyl, i-butyl, and phenyl. Several other nonlimiting examples of R are shown below:

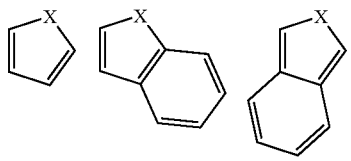

X = N, S

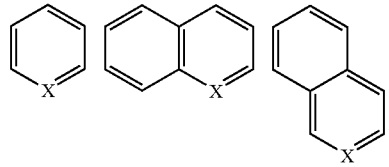

X = C, N

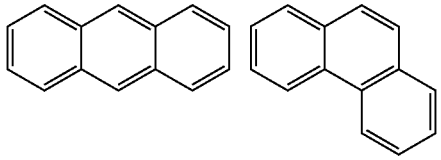

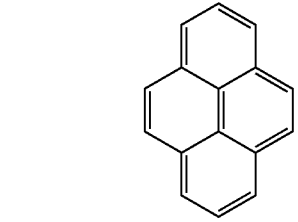

An "m-basic salt", as the term is used herein, is the salt formed from an acid that contains in each molecule m acid groups having a replaceable hydrogen atom.

Various halogenated aromatic acids, to be used as a starting material in the process of this invention, are commercially available. For example, 2-bromobenzoic acid is available from Aldrich Chemical Company (Milwaukee, Wis.). It can be synthesized, however, by oxidation of bromomethylbenzene as described in Sasson et al, *Journal of Organic Chemistry* (1986), 51(15), 2880-2883. Other halogenated aromatic acids that can be used include without limitation 2,5-dibromobenzoic acid, 2-bromo-5-nitrobenzoic acid, 2-bromo-5-methylbenzoic acid, 2-chlorobenzoic acid, 2,5-dichlorobenzoic acid, 2-chloro-3,5-dinitrobenzoic acid, 2-chloro-5-methylbenzoic acid, 2-bromo-5-methoxybenzoic acid, 5-bromo-2-chlorobenzoic acid, 2,3-dichlorobenzoic acid, 2-chloro-4-nitrobenzoic acid, 2,5-dichloroterephthalic acid, 2-chloro-5-nitrobenzoic acid, 2,5-dibromoterephthalic acid, and 2,5-dichloroterephthalic acid, all of which are commercially available. Preferably, the halogenated aromatic acid is 2,5-dibromoterephthalic acid or 2,5-dichloroterephthalic acid.

Other halogenated aromatic acids useful as a starting material in the process of this invention include those shown in the left column of the table below, wherein X=Cl, Br or I, and wherein the corresponding ether of an aromatic acid produced therefrom by the process of this invention is shown in the right column:

| $(COOH)_m-Ar-(X)_n$ I | $(COOH)_m-Ar-(OR)_n$ II |
|---|---|

[Structures of halogenated aromatic acids (left) and corresponding ether derivatives (right), including substituted naphthalenes and benzenes with X and OR groups respectively]

-continued

| $(COOH)_m$—Ar—$(X)_n$ I | $(COOH)_m$—Ar—$(OR)_n$ II |
|---|---|

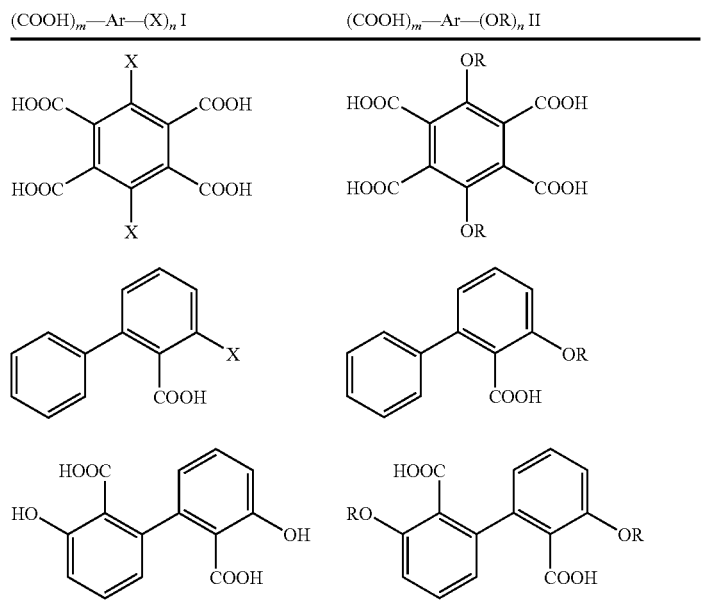

In step (a), a halogenated aromatic acid is contacted with a polar protic or polar aprotic solvent or alcoholic solvent containing the alcoholate $RO^-M^+$, wherein R is as defined above and M is Na or K; a copper (I) or copper (II) source; and a diamine ligand that coordinates to copper.

The alcohol may be ROH, which is preferred, or it may be an alcohol that is not more acidic than ROH. For example, if R is phenyl, such that ROH is phenol, then one nonlimiting example of a less acidic alcohol that can be used in step (a) is isopropanol. Examples of suitable alcohols include without limitation methanol, ethanol, i-propanol, i-butanol, and phenol, with the proviso that the alcohol is either ROH or an alcohol that is not more acidic than ROH.

The solvent may also be a polar protic or polar aprotic solvent or a mixture of protic or polar aprotic solvent. A polar solvent, as used herein, is a solvent whose constituent molecules exhibit a nonzero dipole moment. A polar protic solvent, as used herein, is a polar solvent whose constituent molecules contain an O—H or N—H bond. A polar aprotic solvent, as used herein, is a polar solvent whose constituent molecules do not contain an O—H or N—H bond. Examples of polar solvents other than an alcohol suitable for use herein include tetrahydrofuran, N-methylpyrrolidone, dimethylformamide, and dimethylacetamide.

In step (a), a halogenated aromatic acid is preferably contacted with a total of from about n+m to n+m+1 equivalents of the alcoholate $RO^-M^+$ per equivalent of halogenated aromatic acid. Between m and m+1 equivalents is needed for forming the m-basic salt and between n and n+1 equivalents is needed for the displacement reaction. It is preferred that the total amount of alcoholate not exceed m+n+1. It is also preferred that the total amount of alcoholate not be less than m+n in order to avoid reduction reactions. One "equivalent" as used in this context is the number of moles of alcoholate $RO^-M^+$ that will react with one mole of hydrogen ions; for an acid, one equivalent is the number of moles of acid that will supply one mole of hydrogen ions.

As mentioned above, in step (a), the halogenated aromatic acid is also contacted with a copper (I) or (II) source in the presence of a Schiff base ligand that coordinates to copper.

The copper source and the ligand may be added sequentially to the reaction mixture, or may be combined separately (for example, in a solution of water or acetonitrile) and added together.

The copper source is a Cu(I) salt, a Cu(II) salt, or mixtures thereof. Examples include without limitation CuCl, CuBr, CuI, $Cu_2SO_4$, $CuNO_3$, $CuCl_2$, $CuBr_2$, $CuI_2$, $CuSO_4$, and $Cu(NO_3)_2$. The selection of the copper source may be made in relation to the identity of the halogenated aromatic acid used. For example, if the starting halogenated aromatic acid is a bromobenzoic acid, CuCl, CuBr, CuI, $Cu_2SO_4$, $CuNO_3$, $CuCl_2$, $CuBr_2$, $CuI_2$, $CuSO_4$, and $Cu(NO_3)_2$ will be included among the useful choices. If the starting halogenated aromatic acid is a chlorobenzoic acid, CuBr, CuI, $CuBr_2$ and $CuI_2$ will be included among the useful choices. CuBr and $CuBr_2$ are in general preferred choices for most systems. The amount of copper used is typically about 0.1 to about 5 mol % based on moles of halogenated aromatic acid.

The ligand may be a Schiff base. The term "Schiff base" as used herein denotes a functional group or type of chemical compound containing a carbon-nitrogen double bond with the nitrogen atom connected to an aryl group or an alkyl group but not to hydrogen, such as shown by the structure of Formula IV. It is typically the condensation product of a primary amine and a ketone or aldehyde, produced by a reaction scheme such as the following:

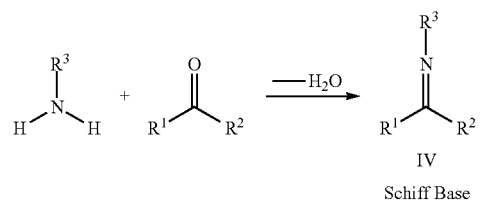

IV
Schiff Base wherein $R^1$, $R^2$ and $R^3$ are each independently selected from substituted and unsubstituted $C_1$-$C_{16}$ n-alkyl, iso-alkyl and tertiary alkyl groups; and substituted and unsubstituted $C_6$-$C_{30}$ aryl and heteroaryl groups.

In one embodiment, a Schiff base suitable for use herein as the ligand includes a diimine such as described generally by Formula V

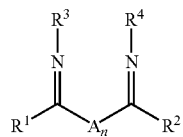

wherein A is selected from the group consisting of

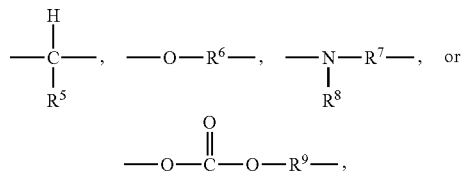

$R^1$, $R^2$, $R^3$ and $R^4$ are each independently selected from substituted and unsubstituted $C_1$-$C_{16}$ n-alkyl, iso-alkyl and tertiary alkyl groups; and substituted and unsubstituted $C_6$-$C_{30}$ aryl and heteroaryl groups;

$R^5$ is selected from H, substituted and unsubstituted $C_1$-$C_{16}$ n-alkyl, iso-alkyl and tertiary alkyl groups; and substituted and unsubstituted $C_6$-$C_{30}$ aryl and heteroaryl groups; and halogen;

$R^6$, $R^7$, $R^8$ and $R^9$ are each independently selected from H or a substituted or unsubstituted $C_1$-$C_{16}$ n-alkyl, iso-alkyl or tertiary alkyl group; and n=0 or 1.

The term "unsubstituted", as used with reference to an alkyl or aryl group in a Schiff base as described above, means that the alkyl or aryl group contains no atoms other than carbon and hydrogen. In a substituted alkyl or aryl group, however, one or more O or S atoms may optionally be substituted for any one or more of the in-chain or in-ring carbon atoms, provided that the resulting structure contains no —O—O— or —S—S— moieties, and provided that no carbon atom is bonded to more than one heteroatom.

In another embodiment, a suitable diimine for use herein as the ligand includes N,N'-dimesityl-2,3-diiminobutane (such as described generally by Formula VI)

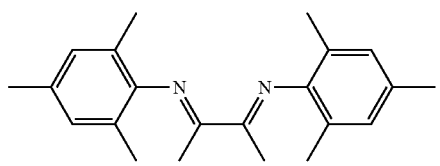

In this instance, n=0, $R^1$=$R^2$=mesityl, and $R^3$ and $R^4$ are taken together to form the $CH_3$—C—C—$CH_3$ moiety bonded to the two nitrogen atoms.

In a further embodiment, a diimine suitable for use herein as the ligand includes N,N'-di(trifluoromethylbenzene)-2,3-diiminoethane (such as described generally by Formula VII)

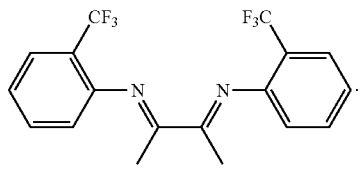

In this instance, n=0, $R^1$=$R^2$=(trifluoromethyl)benzyl, and $R^3$ and $R^4$ are taken together to form the $CH_3$—C—C—$CH_3$ moiety bonded to the two nitrogen atoms.

A ligand suitable for use herein may be selected as any one or more or all of the members of the whole population of ligands described by name or structure above.

Various copper sources and ligands suitable for use herein may be made by processes known in the art, or are available commercially from suppliers such as Alfa Aesar (Ward Hill, Mass.), City Chemical (West Haven, Conn.), Fisher Scientific (Fairlawn, N.J.), Sigma-Aldrich (St. Louis, Mo.) or Stanford Materials (Aliso Viejo, Calif.).

In various embodiments, the ligand may be provided in an amount of about 1 to about 8, preferably about 1 to about 2, molar equivalents of ligand per mole of copper. In those and other embodiments, the ratio of molar equivalents of ligand to molar equivalents of halogenated aromatic acid may be less than or equal to about 0.1. As used herein, the term "molar equivalent" indicates the number of moles of ligand that will interact with one mole of copper.

In step (b), the reaction mixture is heated to form the m-basic salt of the product of step (a), as described by the structure of Formula III:

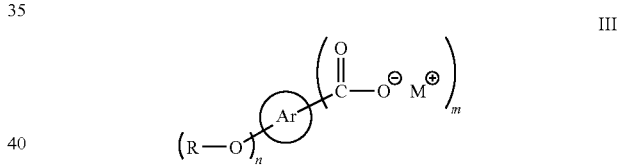

The reaction temperature for steps (a) and (b) is preferably between about 40 and about 120° C., more preferably between about 75 and about 95° C. Typically, the time required for step (a) is from about 0.1 to about 1 hour. The time required for step (b) is typically from about 0.1 to about 1 hour. Oxygen may desirably be excluded during the reaction. The solution is typically allowed to cool before optional step (c) and before the acidification in step (d) is carried out.

The m-basic salt of the ether of the aromatic acid is then contacted in step (d) with acid to convert it to the hydroxy aromatic acid product. Any acid of sufficient strength to protonate the m-basic salt is suitable. Examples include without limitation hydrochloric acid, sulfuric acid and phosphoric acid.

In one embodiment, the copper (I) or copper (II) source is selected from the group consisting of CuBr, $CuBr_2$ and mixtures thereof; the ligand is selected from the group consisting of N,N'-dimesityl-2,3-diiminobutane and N,N'-di(trifluoromethylbenzene)-2,3-diiminoethane; and the copper (I) or copper (II) source is combined with two molar equivalents of the ligand.

The process described above also allows for effective and efficient synthesis of products made from the resulting ethers of aromatic acids such as a compound, a monomer, or an oligomer or polymer thereof. These produced materials may have one or more of ester functionality, ether functionality, amide functionality, imide functionality, imidazole functionality, thiazole functionality, oxazole functionality, carbonate functionality, acrylate functionality, epoxide functionality, urethane functionality, acetal functionality, and anhydride functionality.

Representative reactions involving a material made by the process of this invention, or a derivative of such material, include, for example, making a polyester from the ether of an aromatic acid and either diethylene glycol or triethylene glycol in the presence of 0.1% of $ZN_3(BO_3)_2$ in 1-methylnaphthalene under nitrogen, according to the method taught in U.S. Pat. No. 3,047,536 (which is incorporated in its entirety as a part hereof for all purposes). Similarly, the ether of an aromatic acid is suitable for copolymerization with a dibasic acid and a glycol to prepare a heat-stabilized polyester according to the method taught in U.S. Pat. No. 3,227,680 (which is incorporated in its entirety as a part hereof for all purposes), wherein representative conditions involve forming a prepolymer in the presence of titanium tetraisopropoxide in butanol at 200–250° C., followed by solid-phase polymerization at 280° C. at a pressure of 0.08 mm Hg.

The ether of an aromatic acid can also be polymerized with the trihydrochloride-monohydrate of tetraaminopyridine in a condensation polymerization in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Provisional Application No. 60/665,737, filed Mar. 28, 2005 (which is incorporated in its entirety as a part hereof for all purposes), published as WO 2006/104974. The polymer that may be so produced may be a pyridobisimidazole-2,6-diyl(2,5-dialkoxy-p-phenylene) polymer or a pyridobisimidazole-2,6-diyl(2,5-diareneoxy-p-phenylene) polymer such as a poly(1,4-(2,5-diareneoxy) phenylene-2,6-pyrido[2,3-d: 5,6-d']bisimidazole) polymer. The pyridobisimidazole portion thereof may, however, be replaced by any one or more of a benzobisimidazole, benzobisthiazole, benzobisoxazole, pyridobisthiazole and a pyridobisoxazole; and the 2,5-dialkoxy-p-phenylene portion thereof may be replaced by an alkyl or aryl ether of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole, wherein such an ether is produced according to the methods disclosed herein.

The polymer prepared in such manner may, for example, contain one or more of the following units:

pyridobisimidazole-2,6-diyl(2,5-dialkoxy-p-phenylene) and/or pyridobisimidazole-2,6-diyl(2,5-diphenoxy-p-phenylene) units;

units selected from the group consisting of pyridobisimidazole-2,6-diyl(2,5-dimethoxy-p-phenylene), pyridobisimidazole-2,6-diyl(2,5-diethoxy-p-phenylene), pyridobisimidazole-2,6-diyl(2,5-dipropoxy-p-phenylene), pyridobisimidazole-2,6-diyl(2,5-dibutoxy-p-phenylene) and pyridobisimidazole-2,6-diyl(2,5-diphenoxy-p-phenylene);

pyridobisthiazole-2,6-diyl(2,5-dialkoxy-p-phenylene) and/or pyridobisthiazole-2,6-diyl(2,5-diphenoxy-p-phenylene) units;

units selected from the group consisting of pyridobisthiazole-2,6-diyl(2,5-dimethoxy-p-phenylene), pyridobisthiazole-2,6-diyl(2,5-diethoxy-p-phenylene), pyridobisthiazole-2,6-diyl(2,5-dipropoxy-p-phenylene), pyridobisthiazole-2,6-diyl(2,5-dibutoxy-p-phenylene) and pyridobisthiazole-2,6-diyl(2,5-diphenoxy-p-phenylene);

pyridobisoxazole-2,6-diyl(2,5-dialkoxy-p-phenylene) and/or pyridobisoxazole-2,6-diyl(2,5-diphenoxy-p-phenylene) units;

units selected from the group consisting of pyridobisoxazole-2,6-diyl(2,5-dimethoxy-p-phenylene), pyridobisoxazole-2,6-diyl(2,5-diethoxy-p-phenylene), pyridobisoxazole-2,6-diyl(2,5-dipropoxy-p-phenylene), pyridobisoxazole-2,6-diyl(2,5-dibutoxy-p-phenylene) and pyridobisoxazole-2,6-diyl(2,5-diphenoxy-p-phenylene);

benzobisimidazole-2,6-diyl(2,5-dialkoxy-p-phenylene) and/or benzobisimidazole-2,6-diyl(2,5-diphenoxy-p-phenylene) units;

units selected from the group consisting of benzobisimidazole-2,6-diyl(2,5-dimethoxy-p-phenylene), benzobisimidazole-2,6-diyl(2,5-diethoxy-p-phenylene), benzobisimidazole-2,6-diyl(2,5-dipropoxy-p-phenylene), benzobisimidazole-2,6-diyl(2,5-dibutoxy-p-phenylene) and benzobisimidazole-2,6-diyl(2,5-diphenoxy-p-phenylene);

benzobisthiazole-2,6-diyl(2,5-dialkoxy-p-phenylene) and/or benzobisthiazole-2,6-diyl(2,5-diphenoxy-p-phenylene) units;

units selected from the group consisting of benzobisthiazole-2,6-diyl(2,5-dimethoxy-p-phenylene), benzobisthiazole-2,6-diyl(2,5-diethoxy-p-phenylene), benzobisthiazole-2,6-diyl(2,5-dipropoxy-p-phenylene), benzobisthiazole-2,6-diyl(2,5-dibutoxy-p-phenylene) and benzobisthiazole-2,6-diyl(2,5-diphenoxy-p-phenylene);

benzobisoxazole-2,6-diyl(2,5-dialkoxy-p-phenylene) and/or benzobisoxazole-2,6-diyl(2,5-diphenoxy-p-phenylene) units; and/or units selected from the group consisting of benzobisoxazole-2,6-diyl(2,5-dimethoxy-p-phenylene), benzobisoxazole-2,6-diyl(2,5-diethoxy-p-phenylene), benzobisoxazole-2,6-diyl(2,5-dipropoxy-p-phenylene), benzobisoxazole-2,6-diyl(2,5-dibutoxy-p-phenylene) and benzobisoxazole-2,6-diyl(2,5-diphenoxy-p-phenylene).

EXAMPLES

The advantageous attributes and effects of the processes hereof may be seen in a laboratory example, as described below. The embodiments of these processes on which the example is based are representative only, and the selection of those embodiments to illustrate the invention does not indicate that conditions, arrangements, approaches, steps, techniques, configurations or reactants not described in the example are not suitable for practicing these processes, or that subject matter not described in the example is excluded from the scope of the appended claims and equivalents thereof.

As used herein, the term "conversion" refers to how much reactant was used up as a fraction or percentage of the theoretical amount. The term "selectivity" for a product P refers to the molar fraction or molar percentage of P in the final product mix. The conversion multiplied by the selectivity thus equals the maximum "yield" of P; the actual or "net" yield will normally be somewhat less than this because of sample losses incurred in the course of activities such as isolating, handling, drying, and the like. The term "purity" denotes what percentage of the in-hand, isolated sample is actually the specified substance.

The meaning of abbreviations is as follows "h" means hour(s), "mL" means milliliter(s), "g" means gram(s),

Example 1

In an air and moisture free environment, 4.2 g (77 mmol) of sodium methoxide is combined with 125 g of anhydrous methanol, followed by the addition of 5 g (15 mmol) of 2,5-dibromoterephthalic acid. Separately, 103 mg (0.03 mol equiv) of $CuBr_2$ and 0.06 mol equiv of N,N'-dimesityl-2,3-diiminobutane

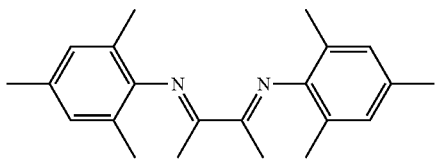

are combined under nitrogen, followed by addition of anhydrous methanol to dissolve. This solution is then added to form the reaction mixture. The reaction mixture is heated to reflux with stirring for 8 h, remaining under a nitrogen atmosphere. After cooling, the product is filtered, washed with hot MeOH and dried to yield a white solid as the bis-sodium salt. The isolated salt is then acidified with hydrochloric acid. The purity is over 95% and the net isolated yield is over 90%.

Each of the formulae shown herein describes each and all of the separate, individual compounds that can be formed in that formula by (1) selection from within the prescribed range for one of the variable radicals, substituents or numerical coefficents while all of the other variable radicals, substituents or numerical coefficents are held constant, and (2) performing in turn the same selection from within the prescribed range for each of the other variable radicals, substituents or numerical coefficents with the others being held constant. In addition to a selection made within the prescribed range for any of the variable radicals, substituents or numerical coefficents of only one of the members of the group described by the range, a plurality of compounds may be described by selecting more than one but less than all of the members of the whole group of radicals, substituents or numerical coefficents. When the selection made within the prescribed range for any of the variable radicals, substituents or numerical coefficents is a subgroup containing (i) only one of the members of the whole group described by the range, or (ii) more than one but less than all of the members of the whole group, the selected member(s) are selected by omitting those member(s) of the whole group that are not selected to form the subgroup. The compound, or plurality of compounds, may in such event be characterized by a definition of one or more of the variable radicals, substituents or numerical coefficents that refers to the whole group of the prescribed range for that variable but where the member(s) omitted to form the subgroup are absent from the whole group.

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, amounts, sizes, ranges and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

Where an embodiment of this invention is stated or described as comprising, including, containing, having, being composed of or being constituted by certain features, it is to be understood, unless the statement or description explicitly provides to the contrary, that one or more features in addition to those explicitly stated or described may be present in the embodiment. An alternative embodiment of this invention, however, may be stated or described as consisting essentially of certain features, in which embodiment features that would materially alter the principle of operation or the distinguishing characteristics of the embodiment are not present therein. A further alternative embodiment of this invention may be stated or described as consisting of certain features, in which embodiment, or in insubstantial variations thereof, only the features specifically stated or described are present.

What is claimed is:

1. A process for preparing an ether of an aromatic acid, the ether being described by the structure of Formula I

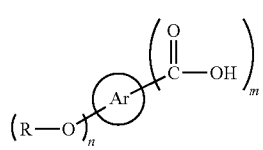

I wherein Ar is a $C_6$–$C_{20}$ monocyclic or polycyclic aromatic nucleus, R is a univalent organic radical, n and m are each independently a nonzero value, and n+m is less than or equal to 8; comprising (a) contacting a halogenated aromatic acid such as is described by the structure of Formula II

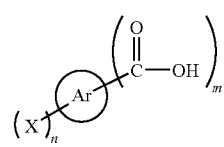

II wherein each X is independently Cl, Br or I, and Ar, n and m are as set forth above, with (i) an alcoholic solvent containing the alcoholate $RO^-M^+$ (wherein M is Na or K);

(ii) a copper (I) or copper (II) source; and (iii) a ligand that coordinates to copper, wherein the ligand comprises a Schiff base;

to form a reaction mixture;
(b) heating the reaction mixture to form the m-basic salt of the product of step (a), as described by the structure of Formula III;

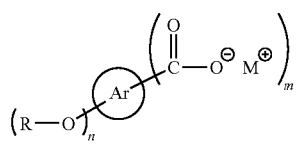
III (c) optionally, separating the Formula III m-basic salt from the reaction mixture in which it is formed; and
(d) contacting the Formula III m-basic salt with acid to form therefrom an ether of an aromatic acid.

2. A process according to claim 1 wherein the halogenated aromatic acid is selected from the group consisting of 2-bromobenzoic acid, 2,5-dibromobenzoic acid, 2-bromo-5-nitrobenzoic acid, 2-bromo-5-methylbenzoic acid, 2-chlorobenzoic acid, 2,5-dichlorobenzoic acid, 2-chloro-3,5-dinitrobenzoic acid, 2-chloro-5-methylbenzoic acid, 2-bromo-5-methoxybenzoic acid, 5-bromo-2-chlorobenzoic acid, 2,3-dichlorobenzoic acid, 2-chloro-4-nitrobenzoic acid, 2,5-dichloroterephthalic acid, 2-chloro-5-nitrobenzoic acid, 2,5-dibromoterephthalic acid, and 2,5-dichloroterephthalic acid.

3. A process according to claim 1 wherein, in step (a), a total of about n+m to n+m+1 normal equivalents of RO⁻M⁺ are added to the reaction mixture per equivalent of the halogenated aromatic acid.

4. A process according to claim 1 wherein the copper source comprises a Cu(I) salt, a Cu(II) salt, or a mixture thereof.

5. A process according to claim 4 wherein the copper source is selected from the group consisting of CuCl, CuBr, CuI, Cu$_2$SO$_4$, CuNO$_3$, CuCl$_2$, CuBr$_2$, CuI$_2$, CuSO$_4$, Cu(NO$_3$)$_2$, and mixtures thereof.

6. A process according to claim 1 wherein the ligand is described by the structure of Formula IV.

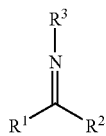
IV wherein R$^1$, R$^2$ and R$^3$ are each independently selected from substituted and unsubstituted C$_1$-C$_{16}$ n-alkyl, iso-alkyl and tertiary alkyl groups; and substituted and unsubstituted C$_6$-C$_{30}$ aryl and heteroaryl groups.

7. A process according to claim 1 wherein the ligand is described by the structure of Formula V

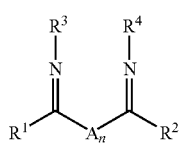
V wherein A is selected from the group consisting of

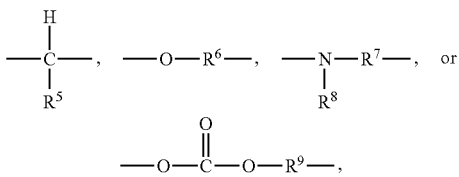

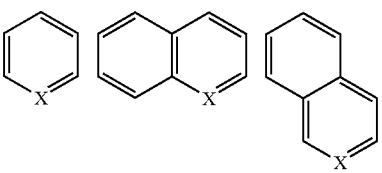

R$^1$, R$^2$, R$^3$ and R$^4$ are each independently selected from substituted and unsubstituted C$_1$-C$_{16}$ n-alkyl, iso-alkyl and tertiary alkyl groups; and substituted and unsubstituted C$_6$-C$_{30}$ aryl and heteroaryl groups;
R$^5$ is selected from H, substituted and unsubstituted C$_1$-C$_{16}$ n-alkyl, iso-alkyl and tertiary alkyl groups; and substituted and unsubstituted C$_6$-C$_{30}$ aryl and heteroaryl groups; and halogen;
R$^6$, R$^7$, R$^8$ and R$^9$ are each independently selected from H or a substituted or unsubstituted C$_1$-C$_{16}$ n-alkyl, iso-alkyl or tertiary alkyl group; and
n=0 or 1.

8. A process according to claim 7 wherein n=0; or R$^3$ and R$^4$ are taken together to form the CH$_3$—C—C—CH$_3$ moiety bonded to the two nitrogen atoms.

9. A process according to claim 1 wherein the ligand is selected from N,N'-dimesityl-2,3-diiminobutane and N,N'-di(trifluoromethylbenzene)-2,3-diiminoethane.

10. A process according to claim 1 further comprising a step of combining the copper source with the ligand before adding them to the reaction mixture.

11. A process according to claim 5 wherein the copper source comprises CuBr or CuBr$_2$.

12. A process according to claim 1 wherein copper is provided in an amount of between about 0.1 and about 5 mol % based on moles of halogenated aromatic acid.

13. A process according to claim 1 wherein the ligand is provided in an amount of between about one and about two molar equivalents per mole of copper.

14. A process according to claim 1 wherein R is selected from the group consisting of C$_1$-C$_{12}$ alkyl groups, aryl groups and the groups described by the structures of the following formulae:

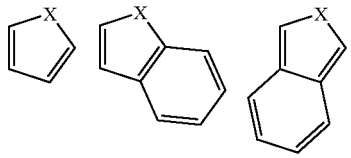
X = N, S

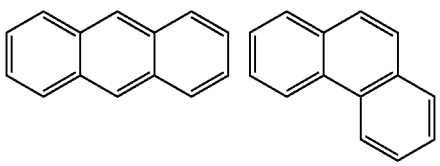
X = C, N

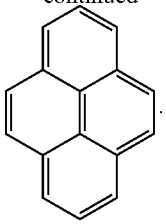

15. A process according to claim 14 wherein R comprises a $C_1 \sim C_4$ alkyl group or phenyl group.

16. A process according to claim 1 wherein the alcoholic solvent comprises ROH.

17. A process according to claim 1 wherein the halogenated aromatic hydroxy acid comprises 2,5-dibromoterephthalic acid or 2,5-dichloroterephthalic acid; R comprises methyl, ethyl, i-propyl, i-butyl or phenyl; the alcoholic solvent comprises ROH or is not more acidic than ROH; the copper source comprises CuBr, $CuBr_2$, or a mixture of CuBr and $CuBr_2$; the copper source is provided in an amount of between about 0.1 and about 5 mol % based on moles of halogenated aromatic acid; the ligand is selected from N,N'-dimesityl-2,3-diiminobutane and N,N'-di(trifluoromethylbenzene)-2,3-diiminoethane; and the ligand is provided in an amount of between about one and about two molar equivalents per mole of copper.

18. A process according to claim 1 further comprising a step of subjecting the ether of the aromatic acid to a reaction to prepare therefrom a compound, monomer, oligomer or polymer.

19. A process according to claim 18 wherein a polymer prepared comprises at least one member of the group consisting of pyridobisimidazole, pyridobisthiazole, pyridobisoxazole, benzobisimidazole, benzobisthiazole, and benzobisoxazole moieties.

20. A process according to claim 19 wherein a polymer prepared comprises a pyridobisimidazole-2,6-diyl(2,5-dialkoxy-p-phenylene) polymer.

* * * * *